(12) United States Patent
Sekiguchi et al.

(10) Patent No.: US 9,244,331 B2
(45) Date of Patent: Jan. 26, 2016

(54) ELECTROMAGNETIC WAVE GENERATING DEVICE, ELECTROMAGNETIC WAVE DETECTING DEVICE, AND TIME-DOMAIN SPECTROSCOPY APPARATUS

(75) Inventors: Ryota Sekiguchi, Kawasaki (JP); Kousuke Kajiki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 243 days.

(21) Appl. No.: 13/818,437

(22) PCT Filed: Aug. 8, 2011

(86) PCT No.: PCT/JP2011/068492
§ 371 (c)(1),
(2), (4) Date: Feb. 22, 2013

(87) PCT Pub. No.: WO2012/029534
PCT Pub. Date: Mar. 8, 2012

(65) Prior Publication Data
US 2013/0146768 A1  Jun. 13, 2013

(30) Foreign Application Priority Data

Aug. 24, 2010 (JP) ................................ 2010-187563
Jul. 22, 2011 (JP) ................................ 2011-161411

(51) Int. Cl.
*G01J 5/00* (2006.01)
*G02F 1/377* (2006.01)
(Continued)

(52) U.S. Cl.
CPC ................ *G02F 1/377* (2013.01); *G01N 21/35* (2013.01); *G01N 21/3586* (2013.01); *G01N 21/4795* (2013.01); *G02F 2001/374* (2013.01); *G02F 2203/13* (2013.01)

(58) Field of Classification Search
CPC . G02F 1/377; G02F 201/374; G02F 2203/13; G01N 21/03; G01N 21/33; G01N 21/475; G01N 21/586

USPC ........................................ 250/338.1; 359/332
See application file for complete search history.

(56) References Cited

U.S. PATENT DOCUMENTS 3,644,846 A * 2/1972 Bridges et al. ................ 359/299
4,446,448 A * 5/1984 Stern ............................. 333/1.1
(Continued)

FOREIGN PATENT DOCUMENTS

EP         1821141 A1    8/2007
WO    2006/062073 A1    6/2006

OTHER PUBLICATIONS

Hebling et al., "Generation of high-power terahertz pulses by tilted-pulse-front excitation and their application possibilities" Journal of Optical Society of America, Jul. 2008, pp. B6-B19, vol. 25, No. 7.
(Continued)

*Primary Examiner* — David Porta
*Assistant Examiner* — Gisselle Gutierrez
(74) *Attorney, Agent, or Firm* — Canon USA Inc. IP Division

(57) ABSTRACT

An electromagnetic wave generating device is provided which includes an optical waveguide including a plurality of waveguide segments such that the main lobe of a combined electromagnetic wave has a substantially single large directivity.

The electromagnetic wave generating device includes the optical waveguide including a plurality of waveguide segments each of which is sandwiched between dielectrics and includes a nonlinear optical crystal. The waveguide segments are arranged such that an angle formed by the directions of propagation of light in the two adjacent waveguide segments substantially corresponds to $2\theta_c$. When $n_g$ denotes the refractive index of the nonlinear optical crystal for light and $\epsilon_{e\!f\!f}$ denotes the effective relative permittivity of an assembly of the dielectrics and the waveguide segments for an electromagnetic wave, $\theta_c$ is defined as $\theta_c = \cos^{-1}(n_g/\theta\sqrt{\epsilon_{e\!f\!f}})$.

18 Claims, 11 Drawing Sheets

(51) Int. Cl.
*G01N 21/3586* (2014.01)
*G01N 21/47* (2006.01)
*G01N 21/35* (2014.01)
*G02F 1/37* (2006.01)

(56) References Cited

U.S. PATENT DOCUMENTS

| | | | | |
|---|---|---|---|---|
| 7,515,801 | B2* | 4/2009 | McCaughan et al. | 385/122 |
| 2003/0137650 | A1* | 7/2003 | Fine et al. | 356/39 |
| 2008/0023632 | A1* | 1/2008 | Ridgway et al. | 250/338.1 |
| 2008/0165355 | A1* | 7/2008 | Yasui et al. | 356/323 |

OTHER PUBLICATIONS

Suizu et al., "Extremely frequency-widened terahertz wave generation using Cherenkov-type radiation", Optics Express, Apr. 2009, pp. 6676-6681, vol. 17, No. 8.
Stepanov et al.,"Efficient generation of subpicosecond terahertz radiation by phase-matched optical rectification using ultrashort laser pulses with tilted pulse fronts", Applied Physics Letters, pp. 3000-3002, Oct. 2003, vol. 83, No. 15.
Stepanov et al.,"THz generation via optical rectification with ultrashort laser pulse focused to a line", Applied Physics B, Feb. 2005, pp. 23-26, vol. 81, No. 1.
Weiss, C., et al., "Generation of tunable narrow-band surface-emitted terahertz radiation in periodically poled lithium niobate", Optics Letters, Apr. 15, 2001, pp. 563-565, vol. 26, No. 8.

* cited by examiner

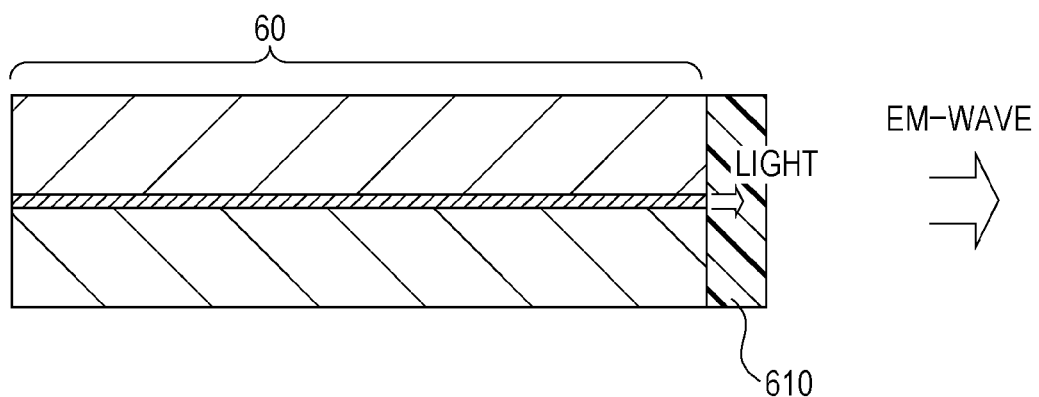
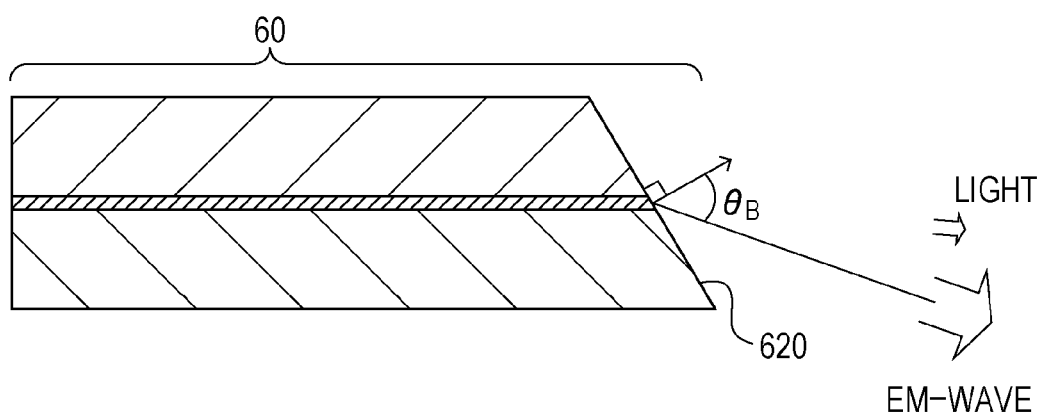

——— WAVE FRONT OF EM1
- - - - WAVE FRONT OF EM2

ELECTROMAGNETIC WAVE GENERATING DEVICE, ELECTROMAGNETIC WAVE DETECTING DEVICE, AND TIME-DOMAIN SPECTROSCOPY APPARATUS

TECHNICAL FIELD

The present invention relates to an electromagnetic wave generating device that generates an electromagnetic wave, such as a terahertz wave, including an electromagnetic wave component in a frequency region ranging from the millimeter waveband to the terahertz waveband (30 GHz to 30 THz), an electromagnetic wave detecting device that detects an electromagnetic wave, such as a terahertz wave, and a time-domain spectroscopy apparatus including the same. In particular, the present invention relates to a generating device (detecting device) including an electro-optical crystal for generation (detection) of an electromagnetic wave including a Fourier component in the frequency band through laser light irradiation, and a tomography apparatus including the same based on terahertz time-domain spectroscopy (THz-TDS).

BACKGROUND ART

In recent years, nondestructive sensing technology using a terahertz wave has been developed. The field of application of electromagnetic waves in this frequency band includes a technique of making a safety imaging and examining apparatus replacing a fluoroscope to perform imaging. Furthermore, a spectroscopic technique for obtaining the absorption spectrum or complex permittivity of a substance to examine physical properties, such as molecular bonds, a measurement technique for examining physical properties, such as carrier density, mobility, and conductivity, and an analysis technique for biomolecules have been developed. As regards a method of generating a terahertz wave, a method using a nonlinear optical crystal has been widely used. Typical examples of nonlinear optical crystals include, for example, $LiNbO_x$ (hereinafter, also referred to as "LN"), $LiTaO_x$, $NbTaO_x$, KTP, DAST, ZnTe, GaSe, GaP, and CdTe. To generate a terahertz wave, a second-order nonlinear phenomenon is used. A known process is difference frequency generation (DFG) caused by two incident laser beams having different frequencies. In addition, monochromatic terahertz wave generation based on an optical parametric process and a process of generating terahertz pulses via optical rectification caused by femtosecond pulsed laser irradiation are also known.

As for the method of generating a terahertz wave using such a nonlinear optical crystal, electro-optic Cherenkov radiation has recently received attention. This is a phenomenon in that when the propagation group velocity of a laser beam 91 as an excitation source is higher than the propagation phase velocity of a generated terahertz wave, the terahertz wave 92 in conical form is radiated like a shock wave as illustrated in FIG. 9. A radiation angle $\theta_c$ is determined on the basis of the ratio of the refractive index of a terahertz wave in a medium (nonlinear optical crystal) to that of light by the following equation:

$$\cos \theta_c = v_{THz}/v_g = n_g/n_{THz}$$

where $v_g$ denotes the group velocity of excitation light, $n_g$ indicates the group refractive index thereof, $v_{THz}$ denotes the phase velocity of the terahertz wave, and $n_{THz}$ indicates the refractive index thereof. A report has been published (refer to NPL 1) which describes that the Cherenkov radiation phenomenon is used and a femtosecond layer beam having a tilted wave front is allowed to enter LN to cause optical rectification, thus generating terahertz pulses of high strength. In addition, a report has been published (refer to NPL 2) which describes that a slab waveguide having a thickness enough smaller than the wavelength of a terahertz wave to be generated is used to save the need to tilt the wave front and a monochromatic terahertz wave is generated by DFG.

The cases in the above-described Non Patent Literature relate to a proposal in that terahertz wave generation is caused by traveling wave excitation and terahertz waves generated from different wave sources match in phase in the direction of radiation and thus enhance each other to improve extraction efficiency. As regards the characteristics of this radiation method, relatively high efficiency can be provided using a nonlinear optical crystal and terahertz waves of high strength can be generated. In addition, the frequency band of terahertz waves can be widened by selecting absorption in a terahertz region, caused by phonon resonance typical of crystal, on the high frequency side. These techniques allow the generation band to be wider than that in terahertz generation using a photoconductive element and the pulse width can be reduced when terahertz pulses are generated using optical rectification. For example, when these techniques are applied to a terahertz time-domain spectroscopy apparatus, the performance of the spectroscopy apparatus is expected to be improved.

CITATION LIST

Non Patent Literature

NPL 1 J. Opt. Soc. Am. B, vol. 25, pp. B6-B19, 2008
NPL 2 Opt. Express, vol. 17, pp. 6676-6681, 2009

SUMMARY OF INVENTION

Technical Problem

A related-art Cherenkov terahertz wave generating device has two directivities in a plane including an optical waveguide. It is far from easy to use. The present invention provides an electromagnetic wave generating device having a substantially single directivity.

Solution to Problem

According to an aspect of the present invention, an electromagnetic wave generating device including a nonlinear optical crystal which allows light from a light source to propagate therethrough and generating an electromagnetic wave having a wavelength longer than that of the light includes a first dielectric and a second dielectric, and an optical waveguide including a plurality of waveguide segments each of which is sandwiched between the dielectrics and includes the nonlinear optical crystal. When $n_g$ denotes the refractive index of the nonlinear optical crystal for the light, $\mathcal{E}_{eff}$ denotes the effective relative permittivity of an assembly of the dielectrics and the waveguide segments for the electromagnetic wave, and $\theta_c$ is defined as $\theta = \cos^{-1}(n_g/\sqrt{\mathcal{E}_{eff}})$, the waveguide segments are arranged such that an angle formed by the directions of propagation of the light in the two adjacent waveguide segments substantially corresponds to $2\theta_c$.

Advantageous Effects of Invention

According to this aspect of the present invention, since the electromagnetic wave generating device includes the optical waveguide including the waveguide segments arranged such that the angle formed by the directions of propagation of the light in the two adjacent waveguide segments substantially corresponds to $2\theta_c$, the main lobe of a combined electromagnetic wave is allowed to have a substantially single large directivity.

Other aspects of the present invention will be apparent from embodiments described below.

BRIEF DESCRIPTION OF DRAWINGS

FIG. 6A is an elevational view of an electromagnetic wave generating device according to a sixth embodiment of the present invention.

FIG. 6B is an elevational view of the electromagnetic wave generating device according to the sixth embodiment of the present invention.

DESCRIPTION OF EMBODIMENTS

According to an aspect of the present invention, an electromagnetic wave generating device includes an optical waveguide including a plurality of waveguide segments including two waveguide segments arranged such that an angle formed by the directions of propagation of light in the waveguide segments substantially corresponds to the above-described $2\theta_g$. On the basis of such a concept, an electromagnetic wave generating device and an electromagnetic wave detecting device according to embodiments of the present invention have fundamental structures as described in the above-described "Solution to Problem".

Embodiments and an example of the present invention will be described below with reference to the drawings.

First Embodiment

Figure 1A:
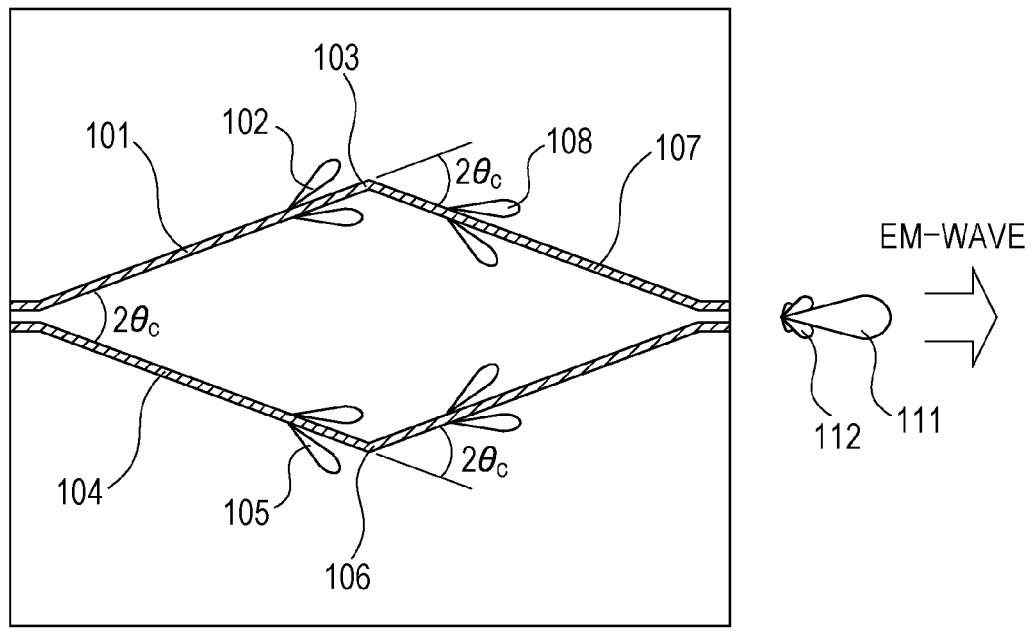
FIG. 1A is a top view of an electromagnetic wave generating device according to a first embodiment of the present invention.
Figure 1B:
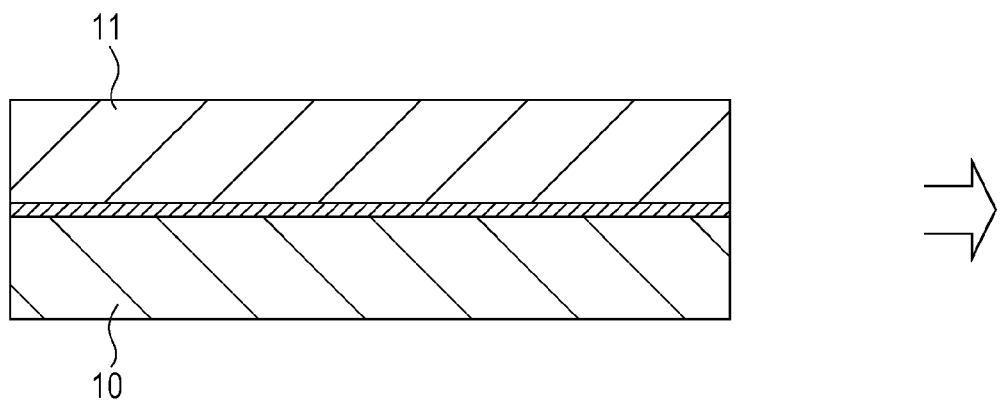
FIG. 1B is an elevational view thereof.

An electromagnetic wave generating device according to a first embodiment will be described with reference to FIGS. 1A and 1B. FIG. 1A is a top view of the electromagnetic wave generating device according to the present embodiment. FIG. 1B is an elevation view thereof. The electromagnetic wave generating device according to the present embodiment includes optical waveguide segments each made of a nonlinear optical crystal and bends connecting the segments. In the present embodiment, an optical waveguide segment 101 has a conical directivity when light propagates therethrough. In a plane of FIG. 1A, the directivity, indicated at 102, appears in two directions. The direction of Cherenkov radiation (hereinafter, "Cherenkov radiation direction") of an electromagnetic wave forms an angle of substantially $\theta_c$, which will be described later, with the direction of propagation of light (hereinafter, "light propagation direction") in the optical waveguide segment 101. The light propagation direction in an optical waveguide segment 104 forms an angle of substantially $2\theta_c$ with that in the optical waveguide segment 101. The optical waveguide segment 104 also has a conical directivity when light propagates therethrough and the directivity, indicated at 105, appears in two directions in the plane. The Cherenkov radiation direction of an electromagnetic wave also forms an angle of $\theta_c$ with the light propagation direction in the optical waveguide segment 104. A bend 103 deflects light propagating through the optical waveguide segment 101 by substantially $2\theta_c$ to guide the light to an optical waveguide segment 107. The light propagation direction in the optical waveguide segment 107 forms an angle of substantially $2\theta_c$ with that in the optical waveguide segment 101 and the optical waveguide segment 107 has a directivity 108 which appears in two directions in the plane when light propagates therethrough. The Cherenkov radiation direction of an electromagnetic wave forms an angle of $\theta_c$ with the light propagation direction in the optical waveguide segment 107. A bend 106 has a function similar to that of the above-described bend 103.

With such a structure, wave components radiated in the same direction from the waveguide segments enhance one another, thus contributing to a main lobe 111 in the directivity of the entire device. Electromagnetic wave components radiated in different directions weaken one another and the wave components which are not completely cancelled become a side lobe 112. The entire device therefore has a substantially single directivity. When excitation light is introduced to an incident end of the waveguide from the left in FIG. 1A, an electromagnetic wave (EM-WAVE) is radiated to the right in FIG. 1A. This is a mechanism whereby the electromagnetic wave generating device according to the embodiment of the present invention has a substantially single directivity represented by the main lobe. According to the present embodiment, the optical waveguide segments are arranged in a rhombus pattern such that an angle formed by the light propagation directions in the two adjacent waveguide segments is substantially $2\theta_c$, thus constituting a structure having a single directivity.

Furthermore, to achieve Cherenkov radiation, the relationship between the velocity $v_g$ of light propagating through the optical waveguide and the phase velocity $v_{THz}$ of a radiated electromagnetic wave, such as a terahertz wave, has to satisfy the condition $v_g > v_{THz}$. The reason is that $\cos^{-1}(v_{THz}/v_g)$ has to have a real root. In the embodiment of the present invention, the Cherenkov radiation of an electromagnetic wave, such as a terahertz wave, far-infrared light, or mid-infrared light, having a wavelength longer than light is caused. A radiated electromagnetic wave therefore has a spatial spread as compared to light. The electromagnetic wave generating device according to the present embodiment includes a first dielectric 10 and a second dielectric 11 vertically sandwiching the optical waveguide, as illustrated in FIG. 1B, to slow the phase velocity of the electromagnetic wave using the above-described difference in spatial spread between the electromagnetic wave and light. In this case, the electromagnetic wave is strongly sensitive to the permittivities of the dielectrics 10 and 11, so that $\theta_c$ is determined by the effective relative permittivity $\in_{eff}$ of the assembly of the dielectrics and the optical waveguide. In other words, it is expressed by the following equation: $\cos \theta_c = n_g/\sqrt{\in_{eff}}$.

When the thickness of the optical waveguide in FIG. 1B is in the limit of lower thickness, the effective relative permittivity $\in_{eff}$ may be approximately expressed by the mean of the permittivities $\in_{10}$ and $\in_{11}$ of the dielectrics 10 and 11. It is expressed by the following expression: $\in_{eff} = (\in_{10} + \in_{11})/2$. A bias in permittivity in the dielectrics 10 and 11 slightly fluctuates the radiation direction in FIG. 1B. The reason is that when the permittivity of the dielectric 11 is higher than that of the dielectric 10, the distribution of an electromagnetic wave mode leans to the dielectric 11. In this case, the first dielectric 10 is a substrate supporting the nonlinear optical crystal and the second dielectric 11 having a relative permittivity higher than that of the substrate is selected. When the dielectric loss of the dielectric 10 is higher than that of the dielectric 11, the dielectric loss can be avoided using the properties. If the dielectrics exhibit the same dielectric loss, the dielectrics 10 and 11 may be made of the same dielectric material 10. In this case, $\in_{eff} = \in_{10}$. Assuming that the dielectric material is selected so that the optical waveguide is a typical single mode waveguide, the optical waveguide has a thickness of about several micrometers at the highest. Since the wavelength of a terahertz wave is enough larger than this value, this approximate expression often holds upon terahertz radiation.

As for an example selected as the dielectric material 10, the refractive index (group refractive index $n_g$) in the near-infrared region of LN as a nonlinear optical crystal described in "Background Art" is about 2. When a dielectric material having a permittivity (relative permittivity) of about 4 or higher is used, therefore, $\cos^{-1}(n_g/\sqrt{\in_{eff}})$ has a real root, so that Cherenkov radiation is achieved. For a terahertz wave, for example, Si or Ge may be used as a dielectric material. A semi-insulating semiconductor substrate or the like may also be used.

An area (not illustrated) other than the optical waveguide sandwiched between the dielectrics 10 and 11 may be filled with, for example, a dielectric or air. To confine light, a material having a refractive index lower than that of the nonlinear optical crystal constituting the optical waveguide may be used. For example, benzocyclobutene (BCB) or polyimide having a refractive index of about 1.5 which is lower than that of LN may be used.

In the above-described case, it is assumed that the thickness of the dielectrics 10 and 11 is in the limit of upper thickness. The thickness thereof may be thinned to some degree. The reason is as follows. When the spatial spread of a radiated electromagnetic wave is larger than the thickness of the dielectrics 10 and 11, the electromagnetic wave is sensitive to the outside air, thus reducing the effective permittivity (effective relative permittivity) $\in_{eff}$. When $\sqrt{\in_{eff}}$ is extremely smaller than $n_g$ such that $\cos^{-1}(n_g/\sqrt{\in_{eff}})$ does not have a real root, however, Cherenkov radiation is not achieved. The spatial spread of a radiated electromagnetic wave may be recognized as the equivalent wavelength ($\lambda/\sqrt{\in_{10}}$) of the electromagnetic wave in the dielectric material 10.

Second Embodiment

Figure 2A:
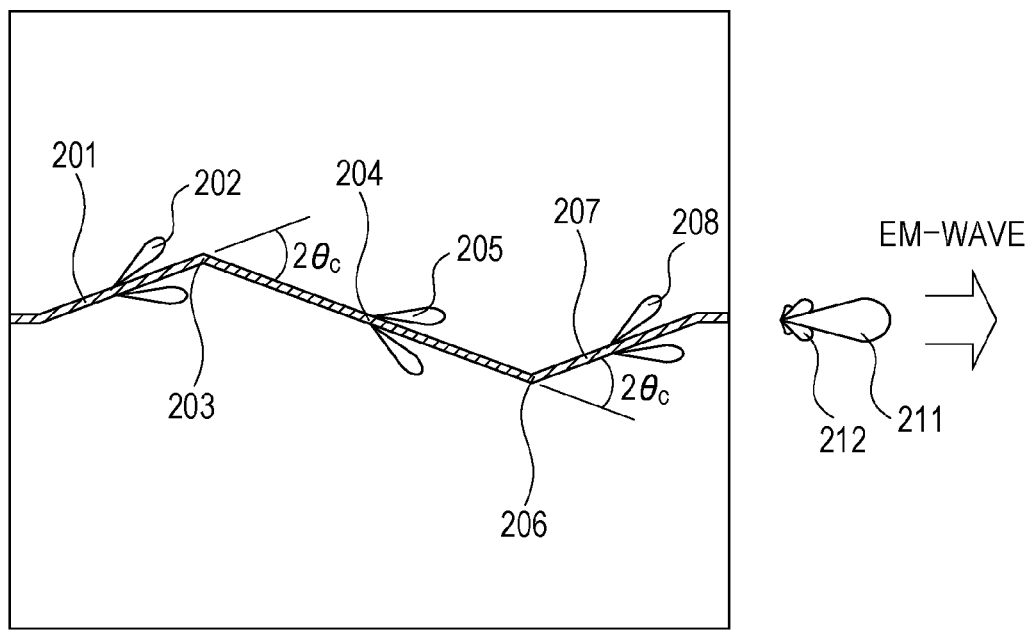
FIG. 2A is a top view of an electromagnetic wave generating device according to a second embodiment of the present invention.
Figure 2B:
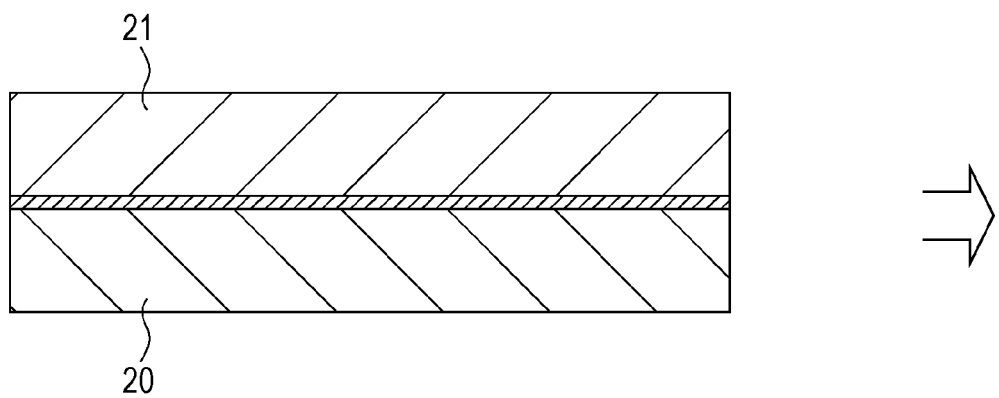
FIG. 2B is an elevational view thereof.

An electromagnetic wave generating device according to a second embodiment will be described with reference to FIGS. 2A and 2B. FIG. 2A is a top view of the electromagnetic wave generating device according to the present embodiment. FIG. 2B is an elevation view thereof. In the present embodiment, optical waveguide segments are connected through bends 203 and 206 to form a single line. Accordingly, light externally enters a single incident end, so that optical coupling is easy. For the rest, the second embodiment is the same as the first embodiment in structure. Referring to FIG. 2A, the light propagation direction in an optical waveguide segment 204 forms an angle of substantially $2\theta_c$ with that in an optical waveguide segment 201 and the light propagation direction in an optical waveguide segment 207 forms an angle of substantially $2\theta_c$ with that in the optical waveguide segment 204. The optical waveguide segments have conical directivities 202, 205, and 208, respectively, when light propagates therethrough. Electromagnetic wave components radiated in the same direction enhance one another, thus contributing to a main lobe 211 in the directivity of the entire device. The entire device therefore has a substantially single directivity. Electromagnetic wave components which are not completely cancelled become a side lobe 212. In the present embodiment, the optical waveguide segments are arranged in a waveform pattern such that the light propagation directions in the two adjacent waveguide segments forms an angle of substantially $2\theta_c$, thus constituting a structure having a substantially single directivity. The electromagnetic wave generating device according to the present embodiment also includes dielectrics 20 and 21 vertically sandwiching such an optical waveguide as illustrated in FIG. 2B.

According to the present embodiment and the first embodiment, since the structure can be extended in the lateral direction, the length of interaction between light propagating through the optical waveguide and the nonlinear optical crystal constituting the optical waveguide can be easily extended. Since the light-to-RF conversion efficiency with which excitation light is converted to an electromagnetic wave (RF) is increased, the embodiments are suitable for apparatuses and applications requiring the light-to-RF conversion efficiency.

Third Embodiment

Figure 3A:
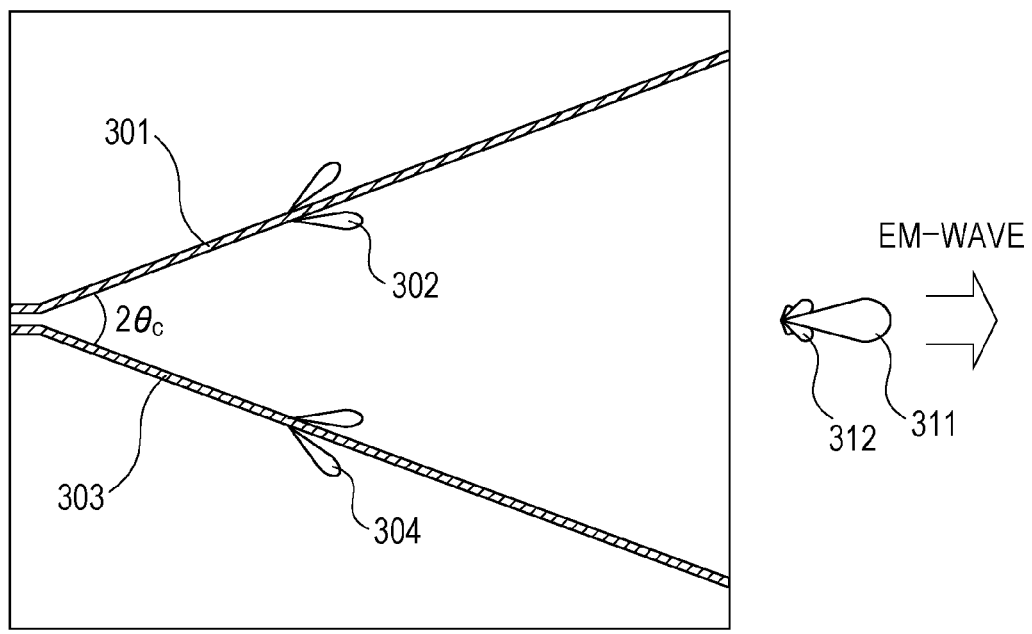
FIG. 3A is a top view of an electromagnetic wave generating device according to a third embodiment of the present invention.
Figure 3B:
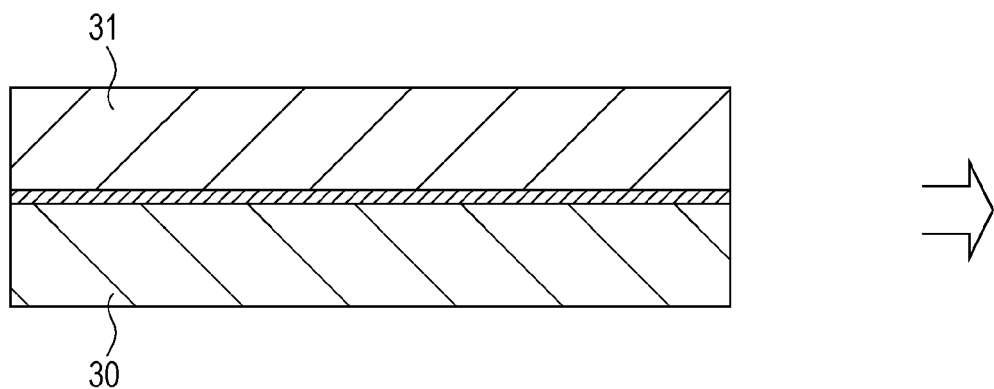
FIG. 3B is an elevational view thereof.

An electromagnetic wave generating device according to a third embodiment will be described with reference to FIGS. 3A and 3B. FIG. 3A is a top view of the electromagnetic wave generating device according to the present embodiment. FIG. 3B is an elevation view thereof. The present embodiment has an advantage in that optical loss caused by a bend does not occur because there is no bend. For the rest, the present embodiment is the same as the first embodiment in structure. Referring to FIG. 3A, the light propagation direction in an optical waveguide segment 303 forms an angle of substantially $2\theta_c$ with that in an optical waveguide segment 301. The optical waveguide segments have conical directivities 302 and 304, respectively, when light propagates therethrough. Electromagnetic wave components radiated in the same direction enhance one another, thus contributing to a main lobe 311 in the directivity of the entire device. Accordingly, the entire device has a substantially single directivity and radiates an electromagnetic wave to the right in FIG. 3A. Electromagnetic wave components which are not completely cancelled become a side lobe 312. According to the present embodiment, the optical waveguide segments forming an angle of substantially $2\theta_c$ are arranged in a V-shaped pattern, thus constituting a structure having a substantially single directivity. The electromagnetic wave generating device according to the present embodiment also includes dielectrics 30 and 31 vertically sandwiching such an optical waveguide as illustrated in FIG. 3B.

In the present embodiment, since light is not collinear with an electromagnetic wave, they can be easily separated from each other. The embodiment is suitable for apparatuses and applications requiring the separation of light and RF.

Fourth Embodiment

Figure 4:
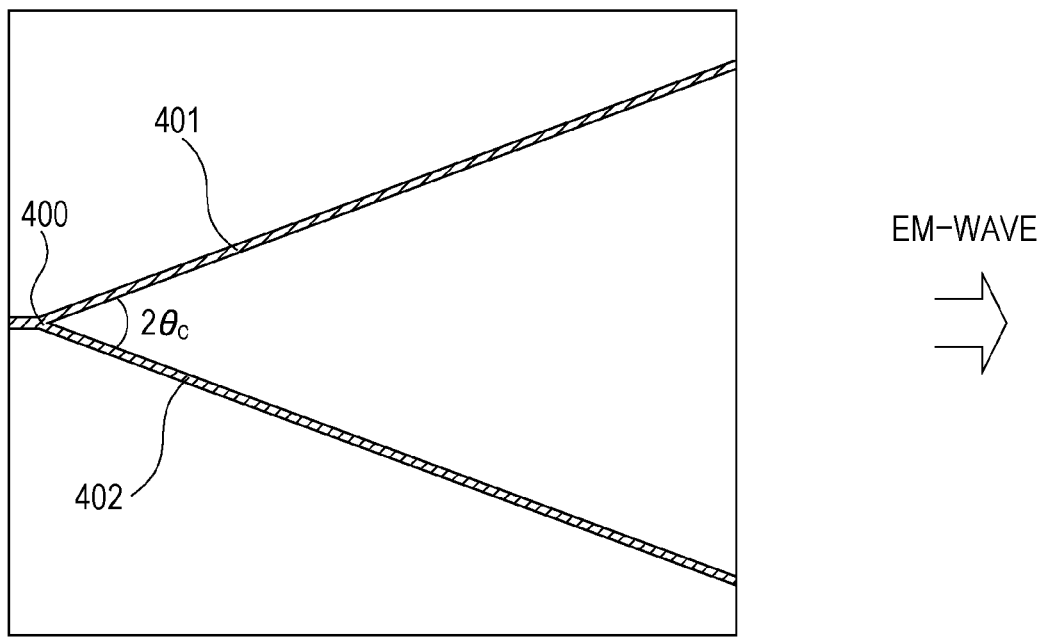
FIG. 4 is a top view of an electromagnetic wave generating device according to a fourth embodiment of the present invention.

In the above-described embodiments, when the optical waveguide of the electromagnetic wave generating device has two incident ends, it is necessary to simultaneously excite the two incident ends with two beams in phase or a single beam having a large spot. FIG. 4 is an electromagnetic wave generating device that includes an optical waveguide having one incident end and a Y-shaped branch 400 on the optical waveguide. The Y-shaped branch 400 does not depend on the wavelength and the polarization direction of light. It is well known as a branch which can be used in a single-mode/multi-mode optical waveguide. A Mach-Zehnder type or the like may be used. The use of this branch can realize an optical waveguide having a structure in which a plurality of small rhomboid patterns are arranged in a rhomboid pattern and an optical waveguide having a structure in which a plurality of V-shaped patterns are arranged in a V-shaped pattern.

Cherenkov radiation is derived from the second-order nonlinear coefficients (d coefficients) of nonlinear optical crystals 401 and 402, although no mention has been made about it. In order to combine the directivities of electromagnetic wave components, it is therefore necessary to pay attention to the direction of the d coefficient of each crystal. More precisely, the d coefficient is a tensor. It is necessary to pay attention to a direction indicated by, for example, i in a d coefficient $d_{i1}$. In the present embodiment in which one beam excites the nonlinear optical crystals 401 and 402, simply, the d coefficients of all the nonlinear optical crystals may indicate a direction perpendicular to the plane illustrated in FIG. 4.

A short pulse laser beam may be used for optical excitation of the above-described electromagnetic wave generating devices. In this case, wide-band electromagnetic pulses having a wavelength longer than that of light can be generated by optical rectification. Two laser beams having different wavelengths may be allowed to enter the device, thus generating an electromagnetic wave having a single frequency which corresponds to the difference between the frequencies and having a wavelength longer than that of light. In the present embodiment and the third embodiment, when two beams are allowed to simultaneously enter two separated optical waveguide segments, the incident end and the emitting end of the optical waveguide can be reversed. The structures according to the above-described embodiments may be used in combination within the bounds of possibility. For example, the present embodiment and the first embodiment may be used in combination such that the structure according to the present embodiment is applied to the left half of the structure according to the first embodiment.

Fifth Embodiment

Figure 5A:
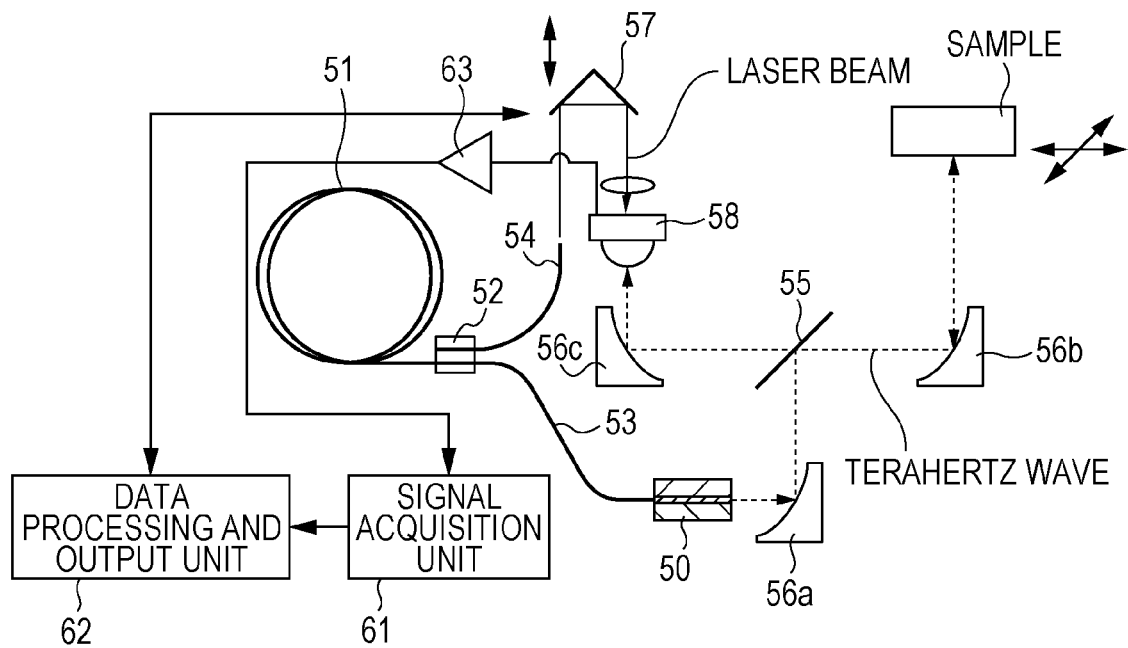
FIG. 5A is a diagram illustrating the structure of a terahertz time-domain spectroscopy apparatus according to a fifth embodiment of the present invention.

FIG. 5A illustrates a tomographic imaging apparatus based on the terahertz time-domain spectroscopy (THz-TDS) system including any of the devices according to the above-described embodiments as an electromagnetic wave generating device. In this apparatus, a femtosecond laser 51 including an optical fiber is used as an excitation light source and output is extracted from fibers 53 and 54 through a branch unit 52. Typically, light having a central wavelength of 1.55 µm, a pulse width of 20 fs, and a repetition frequency of 50 MHz is used. A wavelength in the band of 1.06 µm may be used. The pulse width and the repetition frequency are not limited to these values. Each of the fibers 53 and 54, serving as output stages, may include a dispersion fiber for prechirping to compensate for dispersion by, for example, optical devices including a high nonlinear fiber, disposed at the final stage, for high-order soliton compression, a terahertz generator, and a terahertz detector. Each of these fibers may include a polarization maintaining fiber.

An output from the fiber 53 on the terahertz wave generation side is connected to a waveguide of a Cherenkov radiation type device 50 according to any of the embodiments of the present invention. In this case, the end of the fiber may be integrated with a cylindrical lens array or may be processed to be the pigtail type so that the output is less than or equal to the numerical aperture (NA) of the waveguide of the device 50 in order to increase coupling efficiency. The fiber 53 may be spatially connected to the device 50 through a lens (not illustrated). In each of the above-described cases, applying antireflection coating to each of the ends of the fiber and the device results in reduction of Fresnel loss and reduction of unnecessary interference noise. Alternatively, when the fiber 53 and the waveguide of the device 50 are designed such that the NAs and the mode field diameters of them are close to each other, they may be bonded to each other in a butt-coupling manner by butting against each other. In this case, proper selection of an adhesive can reduce adverse effects of reflection. If the fiber 53 or the fiber laser 51 on the upstream side includes a fiber segment which is not the polarization maintaining type, the polarization of light incident on the Cherenkov radiation type device 50 may be stabilized by an inline polarization controller. The excitation light source is not limited to the fiber laser. When the excitation light source is not a fiber laser, measures to stabilize the polarization are reduced.

A generated electromagnetic wave is detected by a mechanism based on the well-known THz-TDS system illustrated in FIG. 5A. Specifically, a parabolic mirror 56a transforms the beam to a parallel beam, a beam splitter 55 splits the beam into two beams, and a parabolic mirror 56b applies one of the beams to a sample. A parabolic mirror 56c converges an electromagnetic wave reflected from the sample. The resultant wave reaches or is received by a detector 58, including a photoconductive element. The photoconductive element typically includes low temperature grown GaAs and a dipole antenna disposed thereon. If the light source 51 has a wavelength of 1.55 µm, a harmonic wave is generated using an SHG crystal (not illustrated) and is used as probe light for the detector 58. In this case, periodically poled lithium niobate (PPLN) having a thickness of about 0.1 mm may be used in order to maintain a pulse shape. When the light source 51 has a wavelength in the 1-µm band, it is unnecessary to generate a harmonic wave in the detector 58, including a photoconductive element which includes single-layer InGaAs or InGaAs MQW. A reference wave may be used as probe light. In this apparatus, a signal acquisition unit 61 acquires a signal detected by the detector 58 through an amplifier 63. A data processing and output unit 62 includes a PC or the like and obtains the waveform of an electromagnetic wave signal while moving an optical delay 57, serving as a delay unit. Any delay unit may be used so long as the unit can adjust the time of delay between the time of generation of an electromagnetic wave by the device 50, serving as a generating unit, and the time of detection of the electromagnetic wave by the detector 58, serving as a detecting unit. As described above, the present apparatus includes the generating unit, including the electromagnetic wave generating device according to any of the embodiments of the present invention, for generating an electromagnetic wave, the detecting unit for detecting the electromagnetic wave radiated from the generating unit, and the delay unit. This apparatus is configured as the tomography apparatus in which the detecting unit detects an electromagnetic wave, radiated from the generating unit and reflected by a sample, and the reflected wave from the sample is analyzed to image the internal structure of the sample.

Figure 5B:
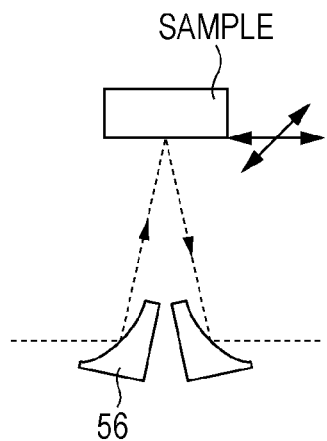
FIG. 5B is a diagram illustrating a modification of the terahertz time-domain spectroscopy apparatus according to the fifth embodiment of the present invention.

In the system illustrated in FIG. 5A, the reflected wave from the sample, serving as a measurement target, is coaxial with the applied electromagnetic wave. The presence of the beam splitter 55 halves the power of the electromagnetic wave. Accordingly, as illustrated in FIG. 5B, the number of mirrors 56 may be increased to provide non-coaxial relationship between the waves so that the power of the electromagnetic wave is increased, though the angle of incidence on the sample is not 90 degrees.

In the use of this apparatus, if a material discontinuity exists in the sample, a reflected echo pulse appears in a time position corresponding to the discontinuity in an acquired signal. When the sample is one-dimensionally scanned, a tomogram is obtained. When the sample is two-dimensionally scanned, a three-dimensional image is obtained. Since the electromagnetic wave generating device 50 including the nonlinear optical crystal is configured as described above, the device has a substantially single directivity, so that antenna gain is increased with the single directivity. Thus, the S/N ratio can be increased. As compared to related art, therefore, a smaller signal can be detected. For example, in the tomography, the thickness of penetration of the sample in the depth direction can be increased. In addition, since a terahertz pulse of relatively short duration, a monopulse of 300 fs or less, can be obtained, depth resolution can be increased. Furthermore, since the excitation laser including a fiber can be used as an irradiating unit, the apparatus can be reduced in size and cost.

Sixth Embodiment

According to the above-described embodiments, the emitting end face of the optical waveguide included in the electromagnetic wave generating device is roughened so that light emitted from the end does not become a noise source, and light is extracted to the outside. FIGS. 6A and 6B illustrate structures for controlling light emitted from the emitting end.

FIG. 6A illustrates an electromagnetic wave generating device 60 whose emitting end is covered by coating 610. As regards coating for optical attenuation, for example, a black polyethylene film can be used. In this case, the thickness of the coating 610 may be equal to or less than one-tenth of the equivalent wavelength of an electromagnetic wave in a material, for example, several micrometers so that the coating does not affect generation of the electromagnetic wave emitted from the emitting end of the device. In a structure having a size that is one-tenth of a wavelength, effects, such as reflection, dispersion, and refraction, on an electromagnetic wave having the wavelength are generally negligible. For this coating, anti-reflection (AR) coating or high-reflection (HR) coating for light may be used. Coating that controls a radiated electromagnetic wave may be used. For example, a Ge film can be used as coating for controlling a terahertz electromagnetic wave while shielding from light.

FIG. 6B illustrates the electromagnetic wave generating device 60 having a bevel 620. Light and an electromagnetic wave can be dispersed using, for example, the difference in angle of refraction between an optical waveguide and the air and the difference in angle of refraction between each dielectric and the air. In this case, if the radiated electromagnetic wave is P polarization, such a cut that the angle of refraction relative to the normal of the bevel 620 corresponds to a Brewster's angle $\theta_B = \tan^{-1}(\sqrt{\in_{\it eff}}/1)$ can be selected. Consequently, Fresnel loss can be reduced in a wider band than that covered by AR coating.

Seventh Embodiment

According to a seventh embodiment, the emitting end of any of the electromagnetic wave generating devices of the embodiments is processed by, for example, AR coating so that light emitted from the emitting end is reused as probe light. Specifically, according to the present embodiment, light emerging from the emitting end of a waveguide included in an electromagnetic wave generating device 70 is allowed to pass through a hole 79 of a parabolic mirror such that a beam corresponding to the optical axis of the light is separated from the light, and the separated beam is used as probe light for a detecting unit. To minimize the diameter of the hole 79 of the parabolic mirror, a small lens (not illustrated) corresponding to the diameter of the beam may be used. A delay unit 77 adjusts the time of delay between the time of arrival of the light at the waveguide in the electromagnetic wave generating device 70 and the time of arrival of the probe light at the detecting unit.

Figure 7:
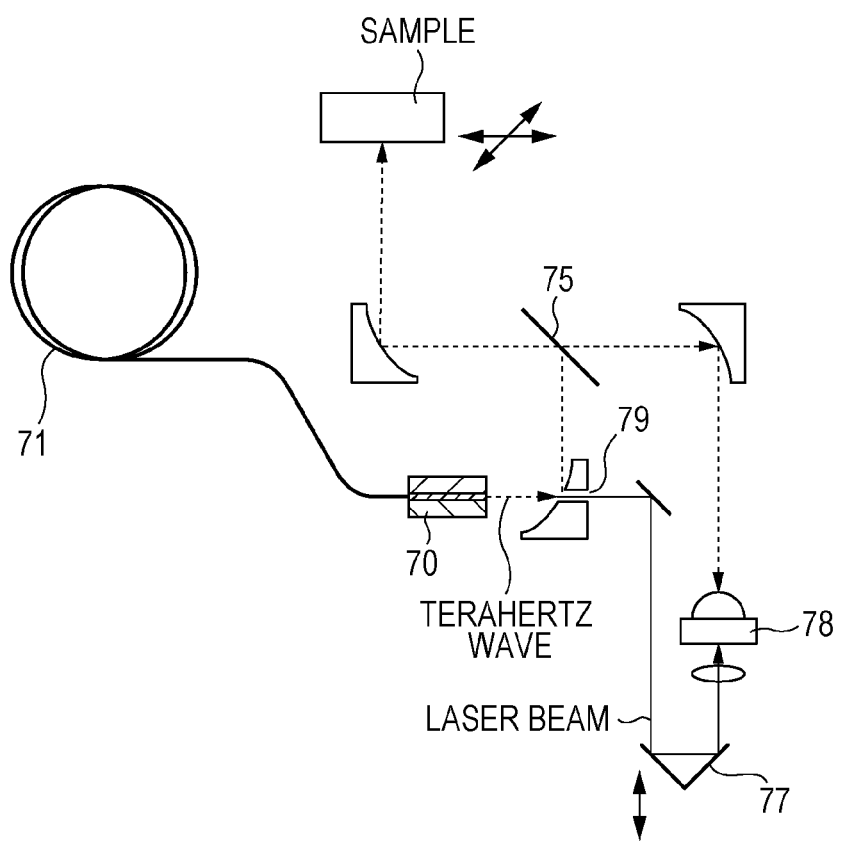
FIG. 7 is a diagram illustrating the structure of a terahertz time-domain spectroscopy apparatus according to a seventh embodiment of the present invention.

FIG. 7 illustrates a tomography apparatus based on the THz-TDS system similar to that in FIG. 5A. Electrical system components are not illustrated in FIG. 7. The present embodiment differs from the fifth embodiment in FIG. 5A in that the apparatus includes no fiber branch unit and the whole of output of an excitation laser 71 including a fiber is allowed to enter the electromagnetic wave generating device 70. A terahertz wave generated from the electromagnetic wave generating device 70 is applied to a sample through parabolic mirrors and a half mirror 75 in a manner similar to the fifth embodiment. Reflected light from the sample enters a terahertz detecting unit 78, thus acquiring a signal. On the other hand, part of the laser beam propagating in the electromagnetic wave generating device 70 again emerges from the emitting end and passes through the hole 79 of the parabolic mirror and the delay unit 77 and is then reused as probe light for the detecting unit 78. In the above-described arrangement, since a branch unit for en excitation laser beam is not needed, the number of components can be reduced and the power of the excitation laser 71 can be efficiently used. The laser source 71 for excitation is not limited to a femtosecond laser source. A KTP-OPO (optical-parametric-oscillator) light source (which outputs light with two wavelengths) for Nd:YAG laser excitation or two tunable laser diodes may be used. Since frequencies for DFG can be changed by changing wavelengths, the frequency of a radiated terahertz wave can also be modulated.

Eighth Embodiment

Figure 10A:
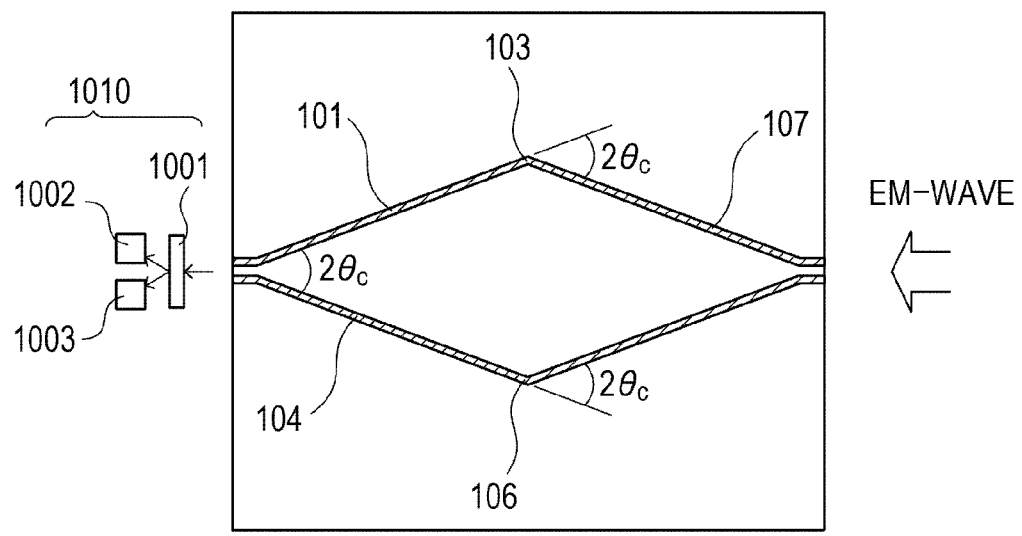
FIG. 10A is a top view of an electromagnetic wave detecting device according to an eighth embodiment of the present invention.

An electromagnetic wave detecting device according to an eighth embodiment will be described with reference to FIGS. 10A and 10B. FIG. 10A is a top view of the electromagnetic wave detecting device according to the present embodiment.

Figure 10B:
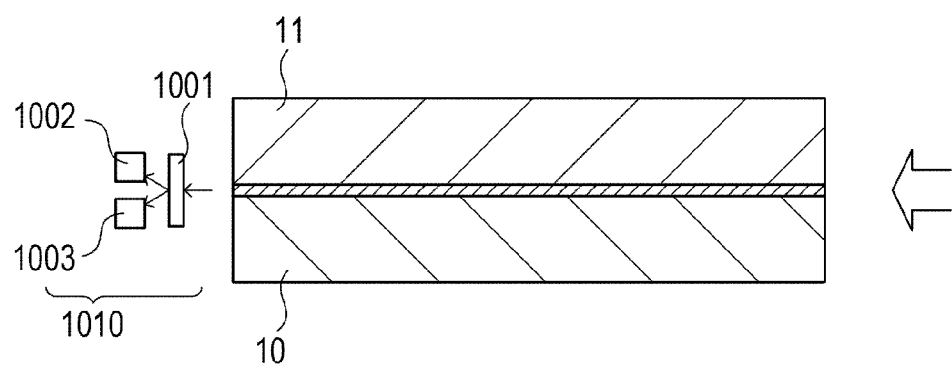
FIG. 10B is an elevational view thereof.

FIG. 10B is an elevation view thereof. The present embodiment relates to the electromagnetic wave generating device that includes the optical waveguide segments 101, 104, and 107, each including an electro-optic crystal, and bends 103 and 106 connecting the segments in a manner similar to the first embodiment and is configured to detect an electromagnetic wave by a reverse process of generation. An electro-optic crystal for the first-order electro-optic effect used here has second-order nonlinearity. A typical practical electro-optic crystal is substantially equivalent to a nonlinear optical crystal having second-order nonlinearity.

In the first embodiment, excitation light is introduced to the incident end of the optical waveguide from the left in FIG. 1A and an electromagnetic wave (e.g., a terahertz wave) is radiated to the right in FIG. 1A. According to the present embodiment, an electromagnetic wave (e.g., a terahertz wave) is detected by the reverse process. Specifically, an electromagnetic wave (e.g., a terahertz wave) is allowed to enter the optical waveguide from the right in FIG. 10A. When probe light is introduced to the incident end of the optical waveguide from the right in FIG. 10A, the probe light is modulated.

A light propagation state detecting unit 1010 is configured to detect a propagation state of the probe light. For example, the state of polarization based on the first-order Pockels effect in the electro-optic crystal is detected by an external polarizing element 1001 and light detecting devices 1002 and 1003 arranged on the outside. Specifically, a Wollaston prism 1001 splits the probe light emerging from the emitting end of the optical waveguide into polarization components, and the S/N ratio is increased by differential amplification through two photodetectors 1002 and 1003, so that the electromagnetic wave can be detected. With this structure according to the present embodiment, the amplitude of the electric field of the electromagnetic wave can be detected.

To compensate for natural birefringence when an electromagnetic wave (e.g., a terahertz wave) is not applied, a phase compensator (e.g., a λ/4 phase shifter) (not illustrated) may be disposed between the emitting end and the polarizing element 1001. Moreover, the above-described light propagation state detecting unit 1010 may be integrated on the optical waveguide.

Figure 11A:
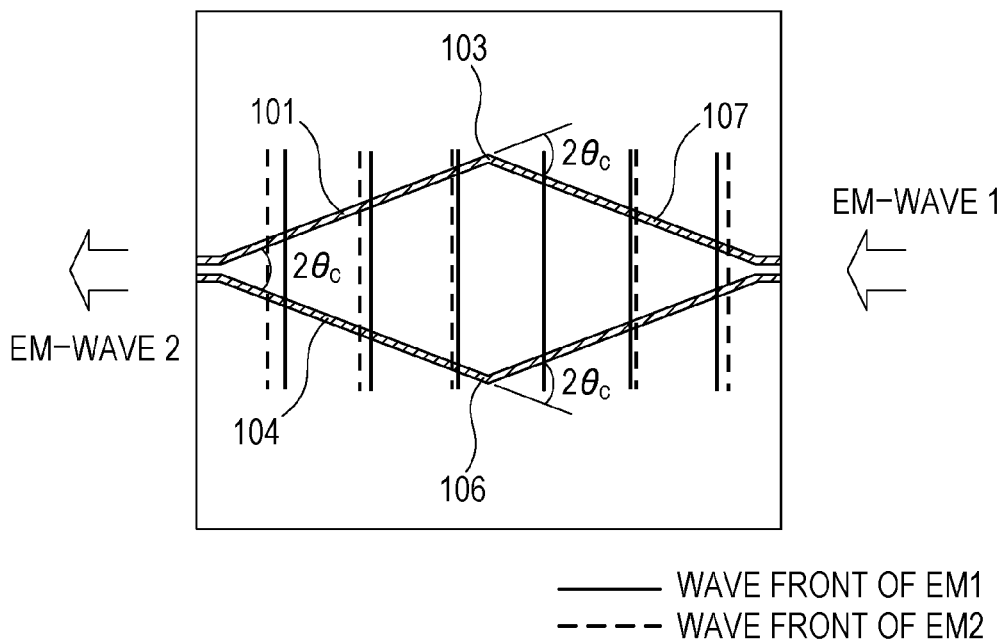
FIG. 11A is a diagram illustrating a method of detection by the electromagnetic wave detecting device.
Figure 11B:
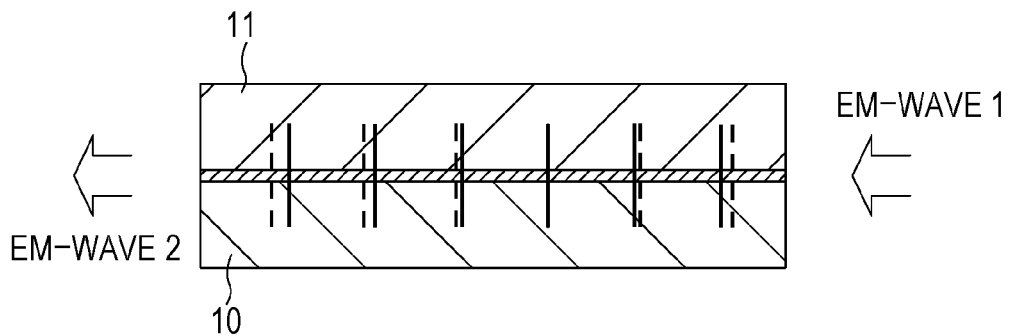
FIG. 11B is a diagram illustrating the method of detection by the electromagnetic wave detecting device.
Figure 11C:
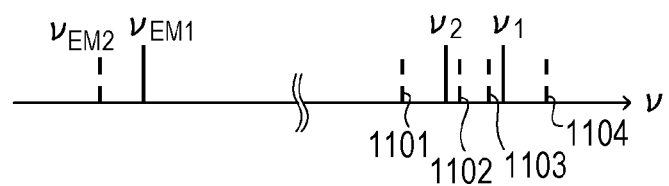
FIG. 11C is a diagram illustrating the method of detection by the electromagnetic wave detecting device.

As regards how to detect an electromagnetic wave (e.g., a terahertz wave), the method of detecting a change of the light polarization state by the first-order electro-optic effect caused by a combined electromagnetic wave has been described. The detection is not limited to this method. A method of detecting a change in phase and intensity of light propagating through the waveguide as a change of the propagation state of light may be used. And a method of detecting an optical beat signal may be used which detects an optical signal indicating the difference between a frequency of light propagating through the optical waveguide and that of a combined electromagnetic wave. An embodiment will be described. According to this embodiment, a device is configured to detect a first electromagnetic wave (EM-WAVE 1 or EM1) and also generate a second electromagnetic wave (EM-WAVE 2 or EM2). In this case, the spectrum $v_{EM1}$ of the first electromagnetic wave and the spectrum $v_{EM2}$ of the second electromagnetic wave may be the same or different from each other. In either case, according to the present embodiment, a region where the wave front of the first electromagnetic wave substantially coincides with that of the second electromagnetic wave is provided as illustrated in FIGS. 11A and 11B. Consequently, a frequency component of $(v_{EM1}-v_{EM2})$ can be superimposed on probe light propagating through the optical waveguide. At this time, the second-order nonlinear effect in the optical waveguide allows the component to be mixed with the probe light. FIG. 11C illustrates a state where the component is mixed with, for example, probe beams having frequencies $v_1$ and $v_2$, serving as two laser beams. In this case, components 1102 and 1104 of $(v_1 \pm v_{EM1}-v_{EM2})$ appear in the side band of the frequency $v_1$ and components 1101 and 1103 of $(v_2 \pm v_{EM1}-v_{EM2})$ appear in the side band of the frequency $v_2$. When the frequencies $v_1$ and $v_2$ and the side bands thereof are observed through, for example, an optical spectrum analyzer, therefore, the first electromagnetic wave can be detected. Furthermore, since the first-order nonlinear effect in the optical waveguide allows the second electromagnetic wave to be modulated by the first electromagnetic wave, the first electromagnetic wave can also be detected by observing the second electromagnetic wave.

In addition, the use of this device allows the construction of the THz-TDS system and the tomography apparatus described in the foregoing embodiments. As regards the generating device in this case, any generating device, e.g., the device based on Cherenkov phase matching described in the embodiments of the present invention or a device using a related-art photoconductive element or the like, may be used.

Example 1

Figure 8A:
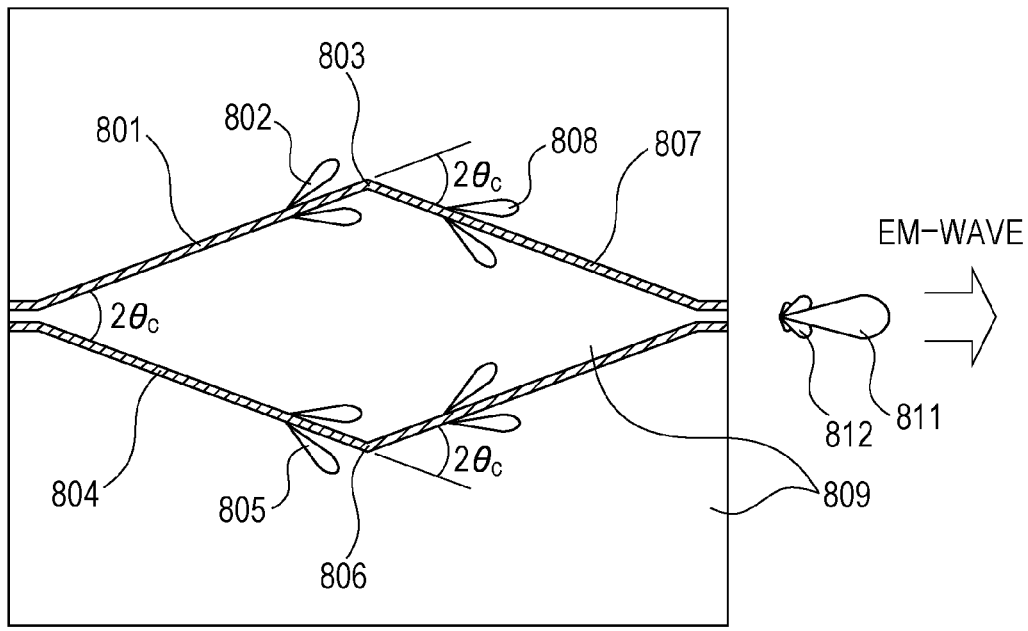
FIG. 8A is a top view of an electromagnetic wave generating device according to Example 1 of the present invention.
Figure 8B:
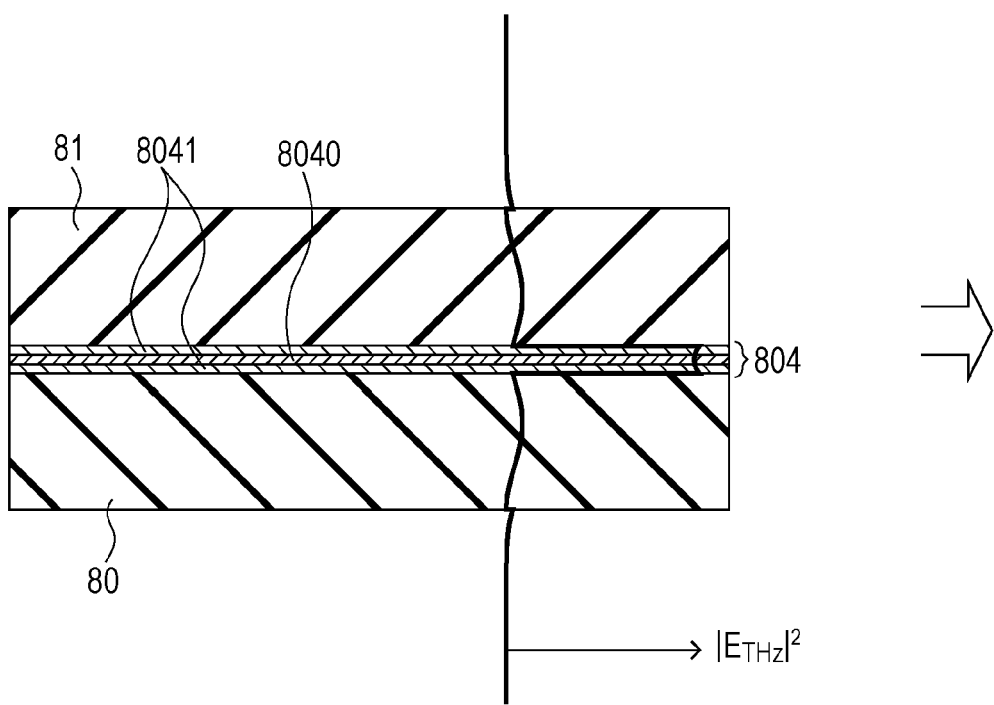
FIG. 8B is an elevational view thereof.
Figure 9:
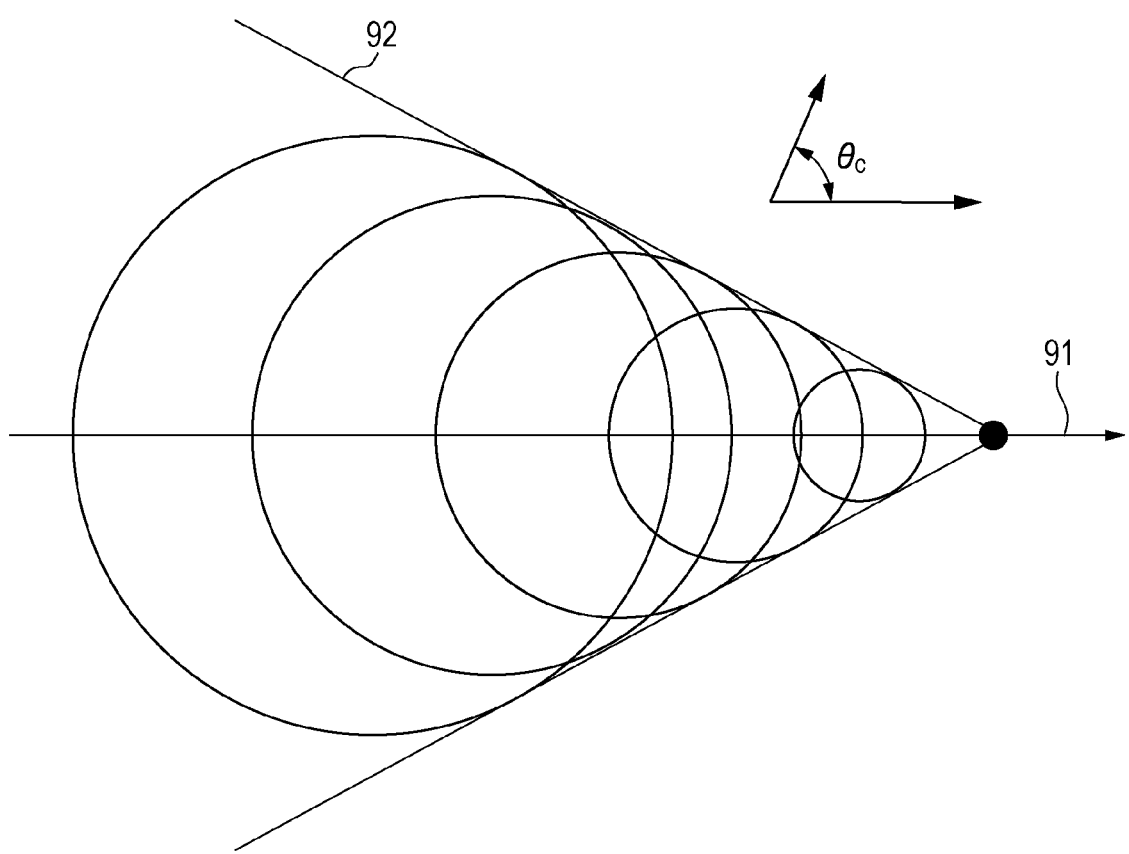
FIG. 9 is a diagram illustrating the principle of electro-optic Cherenkov radiation.

A concrete example 1 corresponding to the first embodiment will be described. An electromagnetic wave generating device according to this example will be described with reference to FIGS. 8A and 8B. FIG. 8A is a top view of the electromagnetic wave generating device according to this example. FIG. 8B is an elevation view thereof.

The device according to this example includes ridge waveguide segments 801, 804, and 807 including ZnTe/CdZnTe and bends 803 and 806 connecting the segments such that the segments are arranged in a rhombus pattern in FIG. 8A. The length of the ridge waveguide segment 804 along a light propagation path is set to, for example, 200 μm and the bend radius of the bend 806 is set to 20 μm at which loss is relatively small. The length and the bend radius are not limited to the values. In this example, if the influence of the bends is eliminated, fundamentally, the half-value angle (angle of spread of part corresponding to half the maximum power of a directivity in FIG. 8A) of a main lobe 811 does not depend on the length of an optical waveguide. To reduce the influence of the bends to sharpen the half-value angle, the length of the optical waveguide may be increased as compared to the bend radius. They are design items. The electromagnetic wave generating device according to this example includes a semiconductor heterostructure of ZnTe (8040)/CdZnTe (8041) on a semi-insulating GaAs substrate 80. The second-order nonlinear coefficient $d_{14}$ of a nonlinear optical crystal ZnTe is relatively high, about 100 μm/V. It is suitable for the band of 1.06 μm and the band of 800 nm. In this example, ZnTe (high refractive index layer) having a refractive index $n_g$=2.8 is used for optical excitation in such a waveband. A semi-insulating GaAs substrate, which is the same material as that for the dielectric 80, is used as a dielectric 81 in FIG. 8B used to sandwich the optical waveguide. An area other than the optical waveguide sandwiched between the dielectrics 80 and 81 is filled with dielectric BCB 809 having a low permittivity and low dielectric loss. Each CdZnTe layer (low refractive index layer) 8041 may be thick enough to function as a clad when light propagates and may be thinned to such extend that the effect of multiple reflection or loss of a terahertz wave is negligible between the GaAs layers 80 and 81. As for the former, in the waveguide including the ZnTe layer 8040 functioning as a core and the CdZnTe layers 8041 functioning as a clad, the CdZnTe layers 8041 may have a thickness equal to or greater than such a thickness that a light intensity at the interfaces with the GaAs layers 80 and 81 is equal to or less than $1/e^2$ (e is the base of a natural logarithm) of a light intensity in the core region. As for the latter, the CdZnTe layer 8041 may have a thickness equal to or less than about 1/10 of the equivalent wavelength $\lambda_{eq}$ of a terahertz wave, having a maximum frequency that is the highest radiation frequency, in the CdZnTe layer 8041.

On the basis of the refractive index ($n_g$=2.8) of the ZnTe layer 8040 and the relative permittivity ($\in_{80}$=$\in_{81}$=12.9) of the semi-insulating GaAs substrates 80 and 81 for a terahertz wave, $\theta_c$ is designed as follows.

$$\theta_c = 38.8 \text{ deg} = \cos^{-1}(n_g/\sqrt{\in_{eff}})$$

Properly speaking, in the use of a refractive index $n_g$=2.77 for the band of 1.06 μm, the designed value is 39.5 deg. In the use of a refractive index $n_g$=2.85 for the band of 800 nm, the designed value is 37.5 deg. Actually, however, if the number of significant digits is two on the basis of the finite half-value angle (angle of spread of part corresponding to half the maximum power in the radiation pattern in FIG. 8A) of each of radiation patterns 802, 805, and 808 in the ridge waveguide having a finite width, an enough design value is obtained. In this example, radiated terahertz wave components in the same direction enhance one another in a manner similar to the first embodiment, thus contributing to the main lobe 811 in the directivity of the entire device. Wave components which are not completely cancelled become a side lobe 812. Accordingly, the entire device has a substantially single directivity, so that the terahertz wave can be radiated to the right in FIG. 8A.

According to another design example, each of the substrates 80 and 81 may be thinned to 60 μm to reduce $\sqrt{\in_{eff}}$. Although a band for Cherenkov radiation is narrowed due to cutoff in a low frequency band or dispersion caused by the size relationship between the spatial spread of an electromagnetic wave and the thickness of each substrate, the decrease of $\theta_c$ reduces bend loss in the bend 806. For example, calculation of a 1-THz electromagnetic wave mode is illustrated. FIG. 8B depicts a calculated distribution of the square of the electric field of the electromagnetic wave. In this case, on the basis of the refractive index ($n_g$=2.8) of ZnTe and the equivalent refractive index ($n_{eq}$=3.04) in the 1-THz electromagnetic wave mode calculated in the above-described structure, $\theta_c$ is designed as follows.

$$\theta_c = 23 \text{ deg} = \cos^{-1}(n_g/n_{eq})$$

The effective permittivity $\in_{eff}$ may be regarded as the square of the equivalent refractive index $n_{eq}$. The effective permittivity can be obtained by such calculation well known to the skilled in the art. This design example is effective in a case where two laser beams having different oscillation frequencies $v_1$ and $v_2$ are allowed to enter a structure so that the structure generates a monochromatic terahertz wave having a frequency difference of $v_1 - v_2$=1 THz.

Such a structure is made such that a semiconductor heterostructure of ZnTe/CdZnTe is formed on the semi-insulating GaAs substrate 80 having a thickness of 525 μm by, for example, molecular beam epitaxy (MBE). Note that the (110) or (111) plane orientation is used so that the nonlinear coefficient $d_{14}$ of each waveguide segment in a direction perpendicular to the plane in FIG. 8B is not zero. As regards crystal growth, on the substrate, the CdZnTe layer 8041 having a thickness of 2 μm, the ZnTe layer 8040 having a thickness of 2 μm, and the CdZnTe layer 8041 having a thickness of 2 μm are formed in that order to epitaxially grow a step index (SI) optical waveguide. After that, etching is performed using a mask of SiO$_2$ or the like to form the ridge waveguide segment 804 having a width of 5 μm. As the width is narrower, it is more ideal. The width may have such an extent that single-mode propagation is achieved. As the width is narrower, the half-value angle of the above-described radiation pattern can be reduced. As for etching, wet etching using, for example, bromine-methanol solution, alternatively, dry etching may be used. Planarization is achieved by applying BCB to an area other than the ridge waveguide segments. Finally, the semi-insulating GaAs substrate 81 is joined to the above components, thus completing the structure according to this example. As regards a method of thinning the substrates 80 and 81, for example, grinding may be performed.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-187563, filed Aug. 24, 2010 and No. 2011-161411, filed Jul. 22, 2011, which are hereby incorporated by reference herein in their entirety.

REFERENCE SIGNS LIST

10, 11 dielectric
101, 104, 107 waveguide segment
102, 105, 108 radiation pattern of waveguide segment
111 main lobe in radiation pattern of entire device
112 side lobe in radiation pattern of entire device

The invention claimed is:

1. An electromagnetic wave generating device that includes a nonlinear optical crystal allowing light from a light source to propagate therethrough and generates an electromagnetic wave having a wavelength longer than that of the light, comprising:
   a first dielectric and a second dielectric; and
   an optical waveguide including a plurality of waveguide segments each of which is sandwiched between the dielectrics and includes the nonlinear optical crystal,
   wherein, when $n_g$ denotes the refractive index of the nonlinear optical crystal for the light, $\in_{eff}$ denotes the effective relative permittivity, $\in_1$ denotes a relative permittivity of the first dielectric, $\in_2$ denotes a relative permittivity of the second dielectric, $\in_{eff}=(\in_1+\in_2)/2$, $n_g<\sqrt{\in_{eff}}$, and $\theta_c=\cos^{-1}(n_g/\sqrt{\in_{eff}})$, the waveguide segments are arranged such that an angle formed by the directions of propagation of the light in two adjacent waveguide segments substantially corresponds to $2\theta_c$.

2. The device according to claim 1, wherein the optical waveguide includes a bend connecting two optical waveguide segments of the waveguide segments.

3. The device according to claim 1, wherein the optical waveguide includes a Y-shaped branch connecting to two optical waveguide segments of the waveguide segments.

4. The device according to claim 1, wherein the thickness of the first and second dielectrics is adjusted such that the value $\theta_c=\cos^{-1}(n_g/\sqrt{\in_{eff}})$ has a real root.

5. The device according to claim 1, wherein
   the first dielectric is a substrate supporting the nonlinear optical crystal, and
   the second dielectric having a relative permittivity equal to or greater than that of the substrate is selected.

6. The device according to claim 1, wherein
the optical waveguide includes a high refractive index layer, serving as a core for the propagating light, and low refractive index layers, serving as a clad,
at least one of the low refractive index layers is in contact with the high refractive index layer and the dielectric, respectively, such that the low refractive index layer is sandwiched therebetween, and
when d denotes the thickness of the low refractive index layer, a denotes a thickness at which the intensity of the light propagating through the optical waveguide at the interface between the low refractive index layer and the dielectric is $1/e^2$ (e is the base of a natural logarithm) of that in the core, and $\lambda_{eq}$ denotes the equivalent wavelength of the electromagnetic wave in the low refractive index layer with a maximum frequency, the thickness d satisfies the condition $a \leq d \leq \lambda_{eq}/10$.

7. A time-domain spectroscopy apparatus comprising:
a generating unit configured to generate an electromagnetic wave;
a detecting unit configured to detect the electromagnetic wave radiated from the generating unit; and
a delay unit configured to adjust the time of delay between the time of generation of the electromagnetic wave by the generating unit and the time of detection of the electromagnetic wave by the detecting unit, wherein
the generating unit includes the electromagnetic wave generating device according to claim 1.

8. An electromagnetic wave detecting device that includes a nonlinear optical crystal allowing light from a light source to propagate therethrough and detects an electromagnetic wave having a wavelength longer than that of the light, comprising:
a first dielectric and a second dielectric; and
an optical waveguide including a plurality of waveguide segments each of which is sandwiched between the dielectrics and includes the nonlinear optical crystal,
wherein, when $n_g$ denotes the refractive index of the nonlinear optical crystal for the light, $\in_{\mathit{eff}}$ denotes the effective relative permittivity $\in 1$ denotes a relative permittivity of the first dielectric, $\in 2$ denotes a relative permittivity of the second dielectric, $\in_{\mathit{eff}} = (\in 1 + \in 2)/2$, $ng = \sqrt{\in_{\mathit{eff}}}$, and $\theta_c = \cos^{-1}(n_g/\sqrt{\in_{\mathit{eff}}})$, the waveguide segments are arranged such that an angle formed by the directions of propagation of the light in two adjacent waveguide segments substantially corresponds to $2\theta_c$.

9. The device according to claim 8, further comprising:
a light propagation state detecting unit configured to detect the state of propagation of the light propagating through the optical waveguide.

10. The device according to claim 9, wherein the light propagation state detecting unit includes a polarizing element and a light detecting device.

11. A time-domain spectroscopy apparatus comprising:
a generating unit configured to generate an electromagnetic wave;
a detecting unit configured to detect the electromagnetic wave radiated from the generating unit; and
a delay unit configured to adjust the time of delay between the time of generation of the electromagnetic wave by the generating unit and the time of detection of the electromagnetic wave by the detecting unit, wherein
the detecting unit includes the electromagnetic wave detecting device according to claim 8.

12. The apparatus according to claim 7, wherein the detecting unit is configured as a tomography apparatus that detects an electromagnetic wave, radiated from the generating unit and reflected by a sample, and analyzes light reflected by the sample to image the internal structure of the sample.

13. The apparatus according to claim 7, wherein light emerging from the emitting end of the optical waveguide of the electromagnetic wave generating device is used as probe light for the detecting unit, and
the delay unit adjusts the time of delay between the time of arrival of the light at the optical waveguide of the electromagnetic wave generating device and the time of arrival of the probe light at the detecting unit.

14. The apparatus according to claim 11, wherein the detecting unit is configured as a tomography apparatus that detects an electromagnetic wave radiated from the generating unit and reflected by a sample, and analyzes light reflected by the sample to image the internal structure of the sample.

15. The device according to claim 1, wherein the electromagnetic wave includes an electromagnetic wave component in a frequency region ranging from 30 GHz to 30 THz.

16. The device according to claim 8, wherein the electromagnetic wave includes an electromagnetic wave component in a frequency region ranging from 30 GHz to 30 THz.

17. The device according to claim 1, wherein the plurality of waveguide segments are straight.

18. The device according to claim 8, wherein the plurality of waveguide segments are straight.

* * * * *